(12) United States Patent  (10) Patent No.: US 9,128,111 B2
Greene et al.  (45) Date of Patent: *Sep. 8, 2015

(54) MONITORING VELOCITY AND DWELL TRENDS FROM WIRELESS SENSOR

(71) Applicant: Intel-GE Care Innovations LLC, Roseville, CA (US)

(72) Inventors: Barry R. Greene, Dublin (IE); Adrian Burns, Killeshandra (IE)

(73) Assignee: INTEL-GE CARE INNOVATIONS LLC, Folsom, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,710

(22) Filed: Jul. 7, 2014

(65) Prior Publication Data

US 2014/0324382 A1  Oct. 30, 2014

Related U.S. Application Data

(63) Continuation of application No. 12/642,964, filed on Dec. 21, 2009, now Pat. No. 8,775,363.

(51) Int. Cl.
*G06N 5/00* (2006.01)
*G06F 1/00* (2006.01)
*G01P 3/64* (2006.01)
*A61B 5/11* (2006.01)
*A61B 5/00* (2006.01)

(52) U.S. Cl.
CPC ............... *G01P 3/64* (2013.01); *A61B 5/1113* (2013.01); *A61B 5/6889* (2013.01); *A61B 2503/08* (2013.01); *A61B 2505/07* (2013.01); *A61B 2562/043* (2013.01)

(58) Field of Classification Search
USPC ............................................. 706/54; 136/66
See application file for complete search history.

(56) References Cited

U.S. PATENT DOCUMENTS

| | | | |
|---|---|---|---|
| 2007/0057786 A1* | 3/2007 | McClure et al. | 340/551 |
| 2009/0196206 A1* | 8/2009 | Weaver et al. | 370/310 |
| 2011/0119267 A1* | 5/2011 | Forman et al. | 707/737 |
| 2011/0184225 A1* | 7/2011 | Whitall et al. | 600/28 |
| 2012/0021873 A1 | 1/2012 | Brunner | |

OTHER PUBLICATIONS

Pavel, Misha, "Unobtrusive Assessment of Mobility", 2006, 5 pages.
Pavel, Misha, "Continuous Assessment of Gait Velocity in Parkinson's Disease from Unobtrusive Measurements", 2007, 4 pages.

* cited by examiner

*Primary Examiner* — Jeffrey A Gaffin
*Assistant Examiner* — Kalpana Bharadwaj
(74) *Attorney, Agent, or Firm* — Pillsbury Winthrop Shaw Pittman LLP

(57) ABSTRACT

A system and method of processing one or more sensor logs includes receiving a sensor log an identifying a set of entries in the sensor log having a predefined sequence of sensor identifiers. The set of entries may define a velocity event. The method can also provide for calculating an in-home gait velocity for the velocity event. In one example, the method also provides for identifying another set of entries in the sensor log having a sensor identifier that corresponds to a dwell sensor mounted in a doorway, wherein the other set of entries define a dwell event. The method may also provide for calculating an in-home dwell time for the dwell event.

21 Claims, 5 Drawing Sheets

MONITORING VELOCITY AND DWELL TRENDS FROM WIRELESS SENSOR

CROSS-REFERENCE TO RELATED APPLICATIONS

This application is related to and claims the benefit under 35 U.S.C. 120 of U.S. application Ser. No. 12/642,964, filed on Dec. 21, 2009, which will issue as U.S. Pat. No. 8,775,363 on Jul. 8, 2014, the entire contents of which is incorporated herein by reference.

BACKGROUND

1. Technical Field

Embodiments generally relate to the monitoring of individual in-home mobility. More particularly, embodiments relate to the measurement of gait velocity and dwell time in a residential setting.

2. Discussion

Falls in the elderly may represent a substantial healthcare problem worldwide. Indeed, a significant percentage of people over seventy years of age experience a significant fall, and the frequency of falls increases with age and the level of frailty. Conventional healthcare solutions may involve conducting manual assessments of patients in clinical environments to obtain estimates of gait velocity, which could be an indicator of frailty and of increased risk of falls. Manual assessments, however, can be labor intensive and time consuming. In addition, clinical systems may be expensive, might not address deployment issues that are unique to in-home deployments, and are therefore typically not scalable to commercial, in-home applications. Moreover, gait velocity estimates may not be accurate and other considerations could also contribute to the frailty determination. Thus, there still remains considerable room for improvement with regard to the monitoring of individual in-home mobility.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Embodiments may provide for a method in which a sensor log is received. The method can include identifying a set of entries in the sensor log having a predefined sequence of sensor identifiers, wherein the set of entries may define a velocity event. The method can further include calculating an in-home gait velocity for the velocity event.

Embodiments may also provide for a computer readable medium comprising a set of stored instructions which, if executed by a processor, cause an apparatus to receive a sensor log and identify a set of entries in the sensor log having a predefined sequence of sensor identifiers, wherein the set of entries are to define a velocity event. The instructions, if executed, may also cause an apparatus to calculate an in-home gait velocity for the velocity event.

In addition, embodiments can include a method in which a sensor log is received, wherein each entry in the sensor log has at least one timestamp. The method may also include identifying a first set of entries in the sensor log having a predefined sequence of sensor identifiers, wherein the first set of entries defines a velocity event for a human subject in an in-home environment. An in-home gait velocity can be calculated for the velocity event based on an initial timestamp in the velocity event, a final timestamp in the velocity event, and a fixed distance between sensors corresponding to the initial and final timestamps. The method may also provide for identifying a second set of entries in the sensor log having a rising edge timestamp, a falling edge timestamp, and a sensor identifier that corresponds to a dwell sensor mounted in a doorway. The second set of entries can define a dwell event for the human subject in the in-home environment. The method may also include calculating an in-home dwell time for the dwell event based on the rising and falling edge timestamps.

Figure 1:
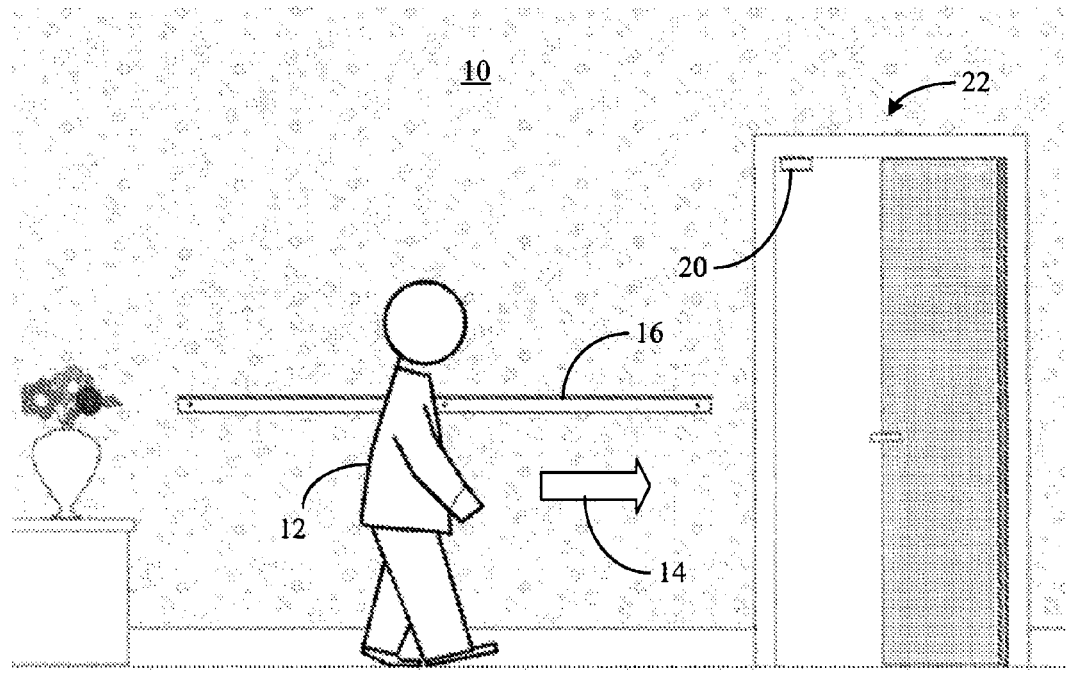
FIG. 1 is a side view of an example of a monitoring scheme in an in-home environment according to an embodiment.
Figure 2:
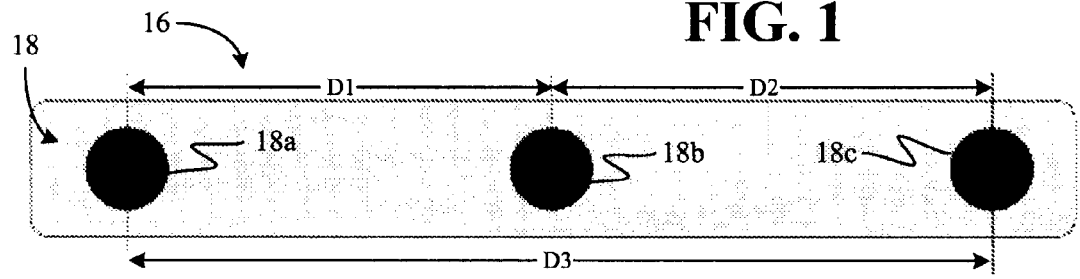
FIG. 2 is a diagram of an example of a plurality of sensors according to an embodiment.
Figure 3:
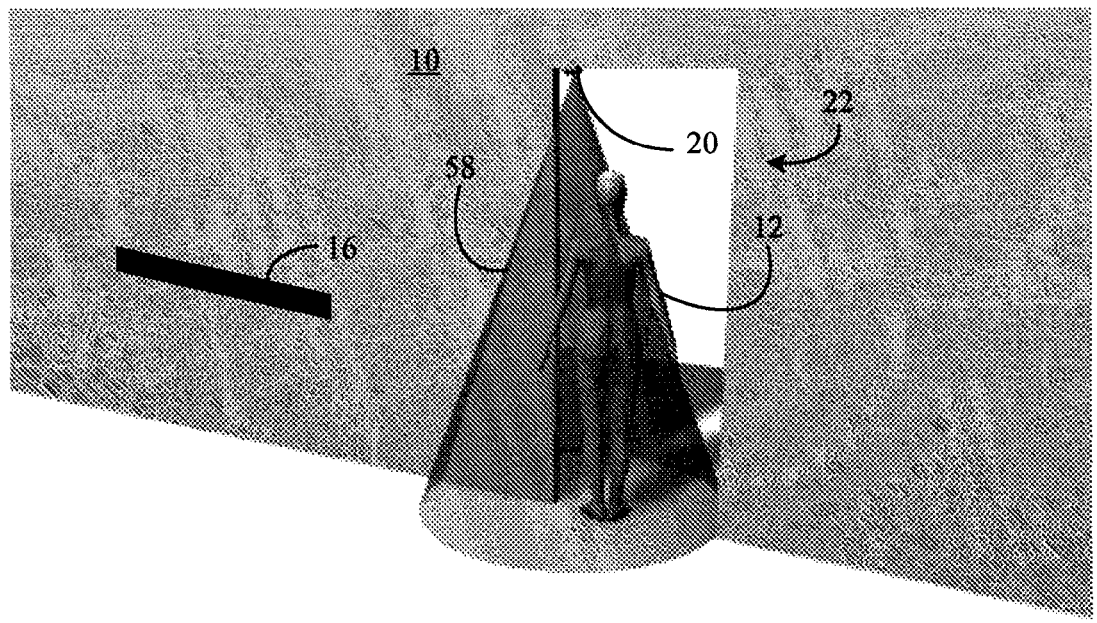
FIG. 3 is a perspective view of an example of monitoring scheme in an in-home environment according to an embodiment.

Turning now to FIGS. 1-3, a home environment 10 is shown in which a human subject 12 walks in a general direction 14 adjacent to a wall-mounted rail 16 and passes through a doorway 22. The illustrated rail 16 has a plurality of passive infrared (PIR) sensors 18 (18a-18c) mounted thereon at known and fixed distances D1, D2 and D3. Each PIR sensor 18 may detect the presence of the subject 12, and trigger the creation of timestamps corresponding to the subject's entry to and exit from the field of sensitivity of the PIR sensor 18 in question. Generally, these timestamps may be transmitted wirelessly to a data aggregator (not shown), which can compile the collected timestamps into a sensor log for further processing and calculation of gait velocities. The rail 16 may also include a processor (not shown), to locally analyze the data generated by the sensors 18 and make gait velocity determinations. In addition, the rail 16 might include a storage medium such as flash memory (e.g., microSD card) to store data generated by the sensors 18. Such an approach may provide a particularly low-cost solution to monitoring individual in-home mobility. The processor could also simply collect the sensor data and transmit it to another location for processing. Additionally, the sensors 18 may share a common clock, which can significantly improve the accuracy of the measurements made by the sensors 18.

The environment 10 may also include a PIR dwell sensor 20 mounted to the doorway 22 to provide data for dwell time measurements. The dwell sensor 20 may, therefore, detect the presence of the subject 12 in the doorway 22, and trigger the creation of timestamps corresponding to the subject's entry to and exit from the field of sensitivity of the dwell sensor 20. Thus, a "rising edge" timestamp could correspond to the subject's entry to the field of sensitivity of the dwell sensor 20, and a "falling edge" timestamp could correspond to the subject's exit from the field of sensitivity of the dwell sensor 20. The data from the dwell sensor 20 measurements may also be transmitted wirelessly to a data aggregator (not shown), for compilation into a sensor log, processing, and calculation of dwell times. The calculated gait velocities and dwell times can provide significant insight into the frailty of the subject 12 in the home environment 10, and therefore provides a unique solution to reducing and/or eliminating the occurrence of falls in the elderly.

Figure 4:
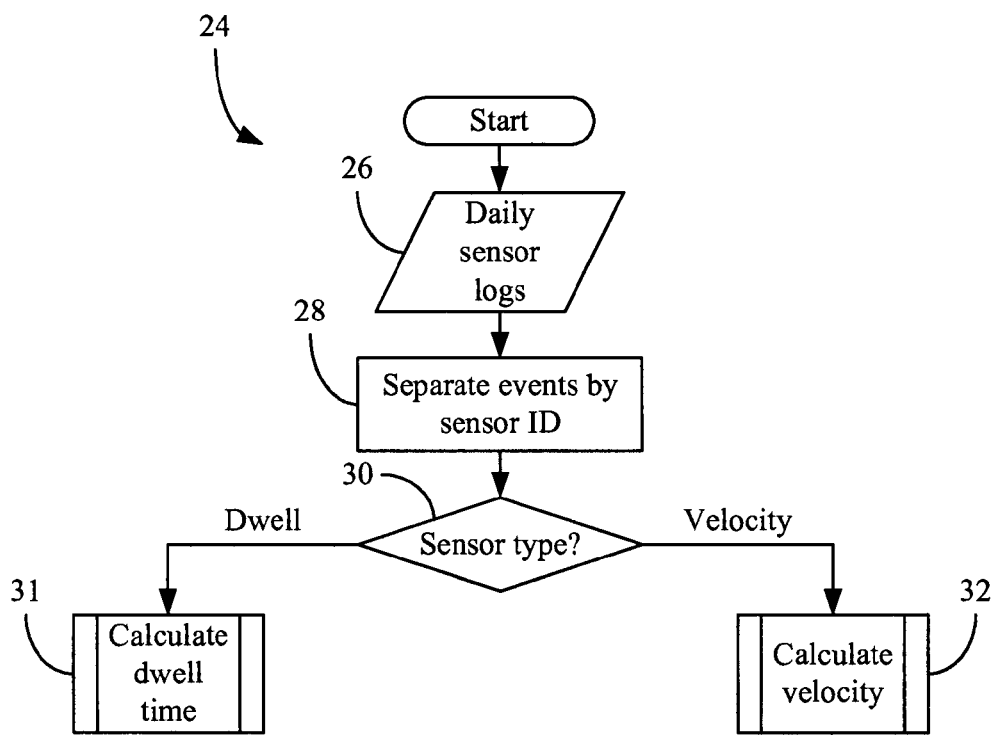
FIG. 4 is a flowchart of an example of a method of processing one or more sensor logs according to an embodiment.

FIG. 4 shows a method 24 of processing sensor data/logs 26. The method 24 may be implemented in executable software as a set of logic instructions stored in a machine- or computer-readable medium of a memory such as random access memory (RAM), read only memory (ROM), programmable ROM (PROM), firmware, flash memory, etc., in fixed-functionality hardware using circuit technology such as application specific integrated circuit (ASIC), complementary metal oxide semiconductor (CMOS) or transistor-transistor logic (TTL) technology, or any combination thereof. For example, computer program code to carry out operations shown in method 24 may be written in any combination of one or more programming languages, including an object oriented programming language such as Java, Smalltalk, C++ or the like and conventional procedural programming languages, such as the "C" programming language or similar programming languages. In addition, one or more of the operations shown in method 24 might be implemented using a commercially available technical computing software product such as Matlab, available from The MathWorks, of Natick, Mass.

As already noted, one or more sensor logs 26 might be generated by a data aggregator or other processing device based on timestamp data obtained from various PIR sensors. An example of such a log is shown below in Table 1.

TABLE 1

| Event# | Sensor ID | Timestamp |
|---|---|---|
| T1 | PIR1 | 2009-12-26 T 06:30:25 |
| T2 | PIR2 | 2009-12-26 T 06:30:28 |
| T3 | PIR3 | 2009-12-26 T 06:30:31 |
| T4 | PIR3 | 2009-12-26 T 07:45:01 |
| T5 | PIR2 | 2009-12-26 T 07:45:02 |
| T6 | PIR1 | 2009-12-26 T 07:45:03 |
| T7 | PIR1 | 2009-12-26 T 07:45:04 |
| T8 | PIR3 | 2009-12-26 T 07:46:00 |
| T9 | PIR4 | 2009-12-26 T 10:15:34 |
| T10 | PIR4 | 2009-12-26 T 10:16:08 |
| T11 | PIR4 | 2009-12-26 T 12:43:59 |
| T12 | PIR4 | 2009-12-26 T 12:43:59 |
| T13 | PIR4 | 2009-12-26 T 12:45:35 |
| T14 | PIR1 | 2009-12-26 T 14:36:00 |
| T16 | PIR2 | 2009-12-26 T 14:36:03 |
| T17 | PIR3 | 2009-12-26 T 14:36:06 |

The particular timestamp values provided in Table 1 are to facilitate discussion only. In addition, the data contained in the sensor log 26 may be structured in any suitable fashion, using a wide variety of fields and/or database structures as appropriate. Indeed, the log 26 may be unstructured raw data obtained directly from the individual sensors. Such a solution may be particularly advantageous in situations where the processing of the data is conducted by a component that is co-located with the sensors on the rail. Notwithstanding, each record/entry in the sensor log 26 may have an event number, a sensor identifier (ID), and one or more timestamps. Processing block 28 provides for receiving the sensor logs and separating events by sensor identifier (ID). A determination can be made at block 30 as to whether a given sensor ID corresponds to a velocity sensor or a dwell sensor. If the sensor is a velocity sensor, block 32 provides for calculating in-home gait velocity. If the sensor is a dwell sensor, block 31 provides for calculating in-home dwell time.

Figure 5:
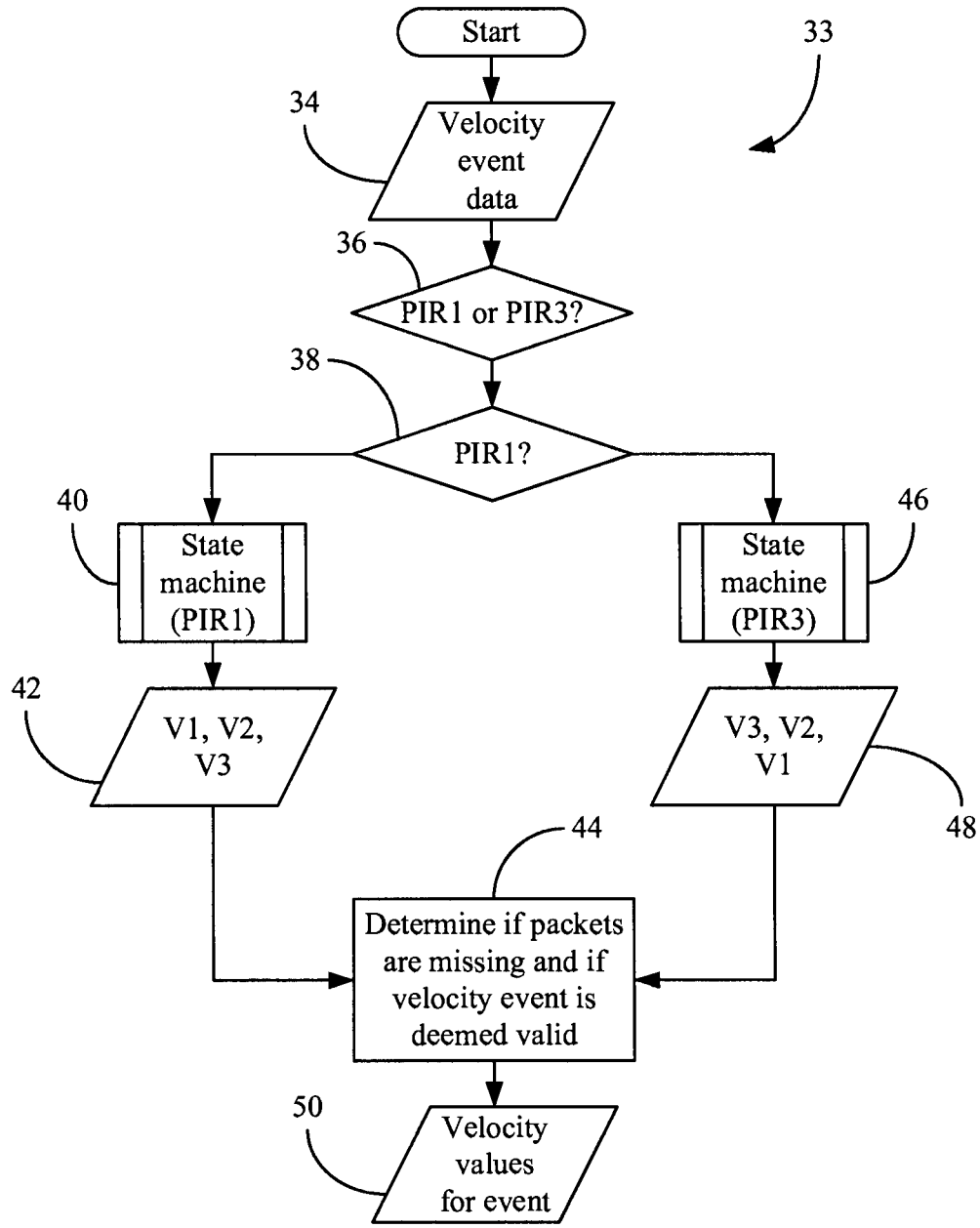
FIG. 5 is a flowchart of an example of a method of calculating gait velocity according to an embodiment.

FIG. 5 demonstrates one approach to calculating in-home gait velocity at process 33. Thus, process 33 may be readily substituted for processing block 32 (FIG. 4), already discussed. In particular, velocity event data 34, which may simply include the entries in the sensor log 26 (FIG. 4) that correspond to velocity sensors, can be used in block 36 to identify the beginning of a predefined sequence of PIR IDs. In the illustrated example, the predefined sequence is either PIR1-PIR2-PIR3, or PIR3-PIR2-PIR1. Thus, block 36 may determine whether the entry in question is either PIR1 or PIR3 (e.g., an identifier corresponding to the beginning of a predefined sequence). If so, block 38 provides for determining which sequence is being processed. If the PIR1-PIR2-PIR3 sequence is being processed, that set of entries defines a velocity event and state machine 40 provides for calculating in-home gait velocities 42 for that velocity event.

Generally, the state machine 40 can consider the timestamp from the first rising edge of PIR1 (e.g., initial timestamp $T_1$) to be the start time of the velocity event (e.g., State I). State II is reached when a valid trigger is received from PIR2 within an acceptable time frame after time $T_1$. Thus, the time of the first rising edge of PIR2 may be reflected in an intermediate timestamp $T_2$. The state machine 40 may enter State III when a valid trigger (e.g., corresponding to final timestamp $T_3$) is received from PIR3 within an acceptable time window from PIR1 and PIR2. The in-home gait velocities may therefore be calculated as follows, $$V_1 = \frac{D_1}{T_2 - T_1} \quad (1)$$

$$V_2 = \frac{D_2}{T_3 - T_2} \quad (2)$$

$$V_3 = \frac{D_3}{T_3 - T_1} \quad (3)$$

Where $D_1$, $D_2$ and $D_3$ are the known and fixed distances between PIR1-PIR2, PIR2-PIR3, and PIR1-PIR3, respectively. Each of these velocity values can have either a negative or positive polarity (indicating direction of movement). The final velocity value (V) for each event may then be calculated as the mean absolute valued velocity for that event, $$V = \frac{\sum_{i=1}^{3} |V_i|}{3} \quad (4)$$

Simply put, the in-home gait velocity for the velocity event can be calculated by averaging a plurality of velocity value calculations (e.g., $V_1$, $V_2$, $V_3$), wherein each velocity value calculation corresponds to a pair of PIR sensors (e.g., PIR1-PIR2, PIR2-PIR3, or PIR1-PIR3) in the predefined sequence (e.g., PIR1-PIR2-PIR3, or PIR3-PIR2-PIR1).

Block 44 demonstrates that there may be certain requirements imposed in order for a given velocity event to be considered valid. For example, the velocity event defined by a particular set of entries can be filtered out (e.g., disqualified) if a velocity disqualification condition, such as the in-home gait velocity exceeding a velocity threshold, is true. Such a velocity threshold can be used in order to identify and discard velocity events that may be physiologically unreasonable. Thus, in the example of Table 1 shown above, the velocity event defined by entries T4, T5 and T6 might be disqualified if a velocity threshold of 4 m/s is used and the distance between PIR1 and PIR3 is nine meters, because there is only a two second differential between the initial timestamp and the final timestamp (i.e., calculated velocity $V_3$ would be 4.5 m/s: nine meters divided by two seconds).

Another example of a velocity disqualification condition might be the time difference between any of the timestamps in a velocity event being less than a velocity refractory/reset threshold. Such a mechanism can prevent spurious triggers from a previous velocity event being counted as part of a valid velocity event (this may arise due to latencies inherent in PIR sensors). For example, in Table 1, entries T6 and T7 for PIR1 are separated by only one second. Thus, entry T7 might be a spurious trigger from entry T6 and inappropriate for inclusion in a valid velocity event. Accordingly, the velocity event that might otherwise be defined by entries T7 and T8, could be disqualified if a velocity reset threshold of two seconds is used.

In fact, because entry T7 is not followed by the appropriate sequence of PIR IDs (e.g., PIR2 is missing), the velocity event may be disqualified on that basis as well. Put another way, the velocity disqualification condition may also include the predefined sequence of PIR IDs not being met. In this regard, missing packets between PIR trigger times could cause spurious velocity values, and may be identified and removed. For example, by examining the event number for each event timestamp, and determining whether the event number between events is incremented by more than one, missing wireless packets may be detected. Thus, in Table 1 above, the velocity event that would normally be defined by entries T14, T16 and T17, might be disqualified because entry T15 is missing and the event could be indicative of one or more missing packets.

If it is determined at block 38 that the PIR3-PIR2-PIR1 sequence (note that the illustrated sequence is bi-directional i.e., can be PIR1-PIR2-PIR3 or PIR3-PIR2-PIR1) is being processed, the illustrated state machine 46 provides for calculating in-home gait velocities 48 for that velocity event using the same equations (1)-(4), as already discussed. After applying the velocity disqualification conditions at block 44, the process 33 may output velocity values 50 for the velocity event. Thus, the illustrated approach provides an automated solution to calculating in-home gait velocity that is accurate, scalable, and takes into consideration wireless deployment issues that may be unique to in-home deployments.

Figure 6:
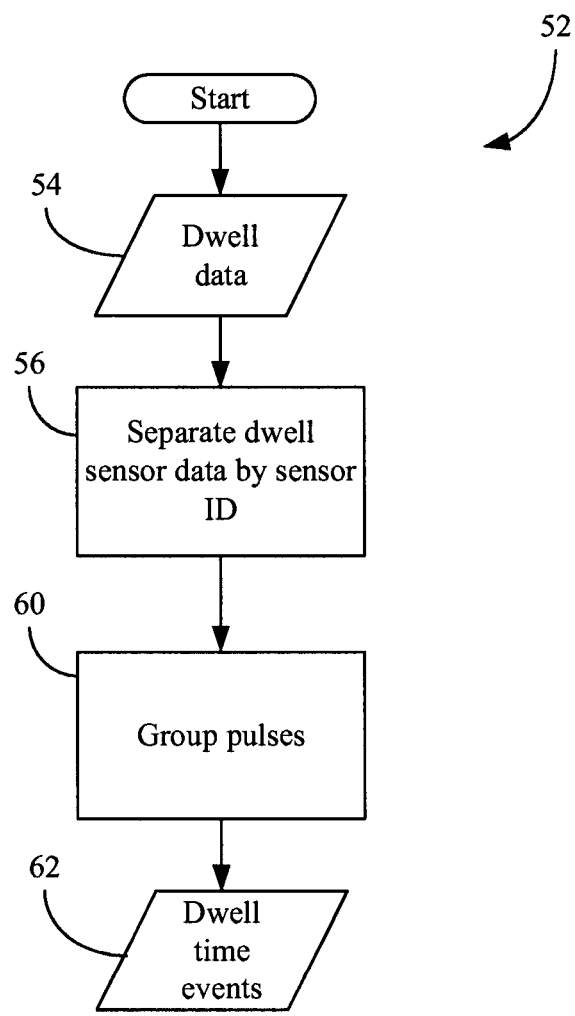
FIG. 6 is a flowchart of an example of a method of calculating dwell time according to an embodiment.

Turning now to FIG. 6, one approach to calculating dwell time is shown in process 52. Thus, process 52 may be readily substituted for processing block 31 (FIG. 4), already discussed. Dwell time, or the time a person spends within the "dwell zone" of a particular PIR sensor, can be calculated from the timestamps generated by each PIR sensor. The dwell zone may be defined as the area within which the subject causes the PIR sensor to trigger. Thus, a dwell zone 58 (FIG. 3) might exist for a certain dwell PIR sensor 20 (FIG. 3) mounted in a doorway. In particular, dwell data 54, which may simply include the entries in the sensor log 26 (FIG. 4) that correspond to dwell sensors, can be separated by sensor ID at block 56. Thus, a set of entries may be identified, wherein the set of entries generally defines a dwell event for the subject in the in-home environment. In particular, the set of entries may include a rising edge timestamp, a falling edge timestamp, and a PIR ID that corresponds to a dwell sensor that is known to be mounted in a doorway. Referring again to Table 1, for example, entries T9 and T10 for PIR4 might be considered as representing a pulse having a rising edge that corresponds to the timestamp of entry T9 and a falling edge that corresponds to the timestamp of entry T10.

Block 60 provides for grouping pulses that are spaced less than a certain time period (say, one second) apart as belonging to the same dwell event. For example, entries T11 and T12 in Table 1 have the same timestamp and therefore may be grouped together into the pulse having a falling edge that corresponds to the timestamp of entry T13. Block 60 may also provide for imposing certain requirements in order for a given dwell event to be considered valid. For example, a dwell event defined by a particular set of entries can be disqualified if a dwell disqualification condition, such as the time difference between the rising edge timestamp and the falling edge timestamp of a previous dwell event being less than a dwell reset threshold, is true. Thus, successive dwell events might be required to be separated by a time value such as least one second in order to be considered valid.

Another example of a dwell disqualification condition might be the time difference between the rising edge timestamp and the falling edge timestamp (e.g., the pulse width) exceeding a dwell duration threshold, such as sixty seconds. Such a technique may prevent the capture of static behavior rather than dynamic behavior. For example, the grouped set of time entries T11, T12 and T13 in Table 1, have a pulse width that is longer than sixty seconds. Accordingly, the dwell event defined by those entries could be disqualified. Yet another example of a dwell disqualification condition could be the time difference between the rising and falling edge timestamps being a negative value, which may also be indicative of spurious behavior. Once the pulse grouping and event disqualification analysis is complete, the illustrated process 52 calculates in-home dwell times 62 for the dwell events based on the appropriate rising and falling edge timestamps.

Thus, the automatic calculation of dwell times can provide information about individual frailty that goes beyond the gait velocity determination. Accordingly, the illustrated approach can be very robust and dependable.

Experimental Results

The above techniques were tested for a number of 'velocity events' or walks the length of a velocity rail in a controlled environment. Data was acquired from a 2 m long velocity rail from five healthy adult subjects (mean age: 31 years). The distance between PIR1 and PIR3 was 1.92 m while the distance between individual PIRs was 0.96 m. Each subject performed four walks. The velocity rail was secured on a wall 1 m above ground level. A line of chairs were placed 1.5 m opposite this rail to simulate the presence of a wall opposite the rail. Each subject was asked to perform the first walk at 'Slow' pace, the second walk at a pace designated as 'Medium' and the final two walks at a pace designated 'Fast'. Data for each walk was captured using PIR sensors and client/server software. The velocity for each walk was manually calculated from the timestamps contained in the server output. In addition, the techniques described above were used to automatically calculate the velocity of each walk. The manually derived velocity for each walk was compared against the velocity value automatically derived by the algorithm. The mean percentage error and intraclass correlation coefficient (ICC(2, k)) were used to perform the comparison. Table 2 below gives the results for each walk for each of the five subjects. For a number of walks, one or more PIRs failed to trigger and so the rail did not provide a timestamp for the moment the participant passed the PIR. These walks are left blank below.

TABLE 2

| | Automatically Calculated Vel. [m/s] | | | | Manually Calculated Vel. [m/s] | | | | Mean Error [%] | ICC (2, k) |
|---|---|---|---|---|---|---|---|---|---|---|
| Sub | Slow | Medium | Fast 1 | Fast 2 | Slow | Medium | Fast 1 | Fast 2 | | |
| 1 | 0.31 | −0.47 | 1.18 | NC | 0.31 | −0.48 | 1.2 | | 1.27 | 0.99 |
| 2 | 0.33 | −0.7 | | NC | 0.34 | −0.71 | | | 1.8 | 0.99 |
| 3 | 0.34 | | | −1.56 | 0.34 | | | −1.59 | 1.72 | 0.99 |
| 4 | 0.33 | −0.8 | | | 0.34 | −0.81 | | | 1.78 | 0.99 |
| 5 | 0.47 | −1.16 | | −1.76 | 0.47 | −1.18 | | −1.79 | 1.79 | 0.99 |

Figure 7:
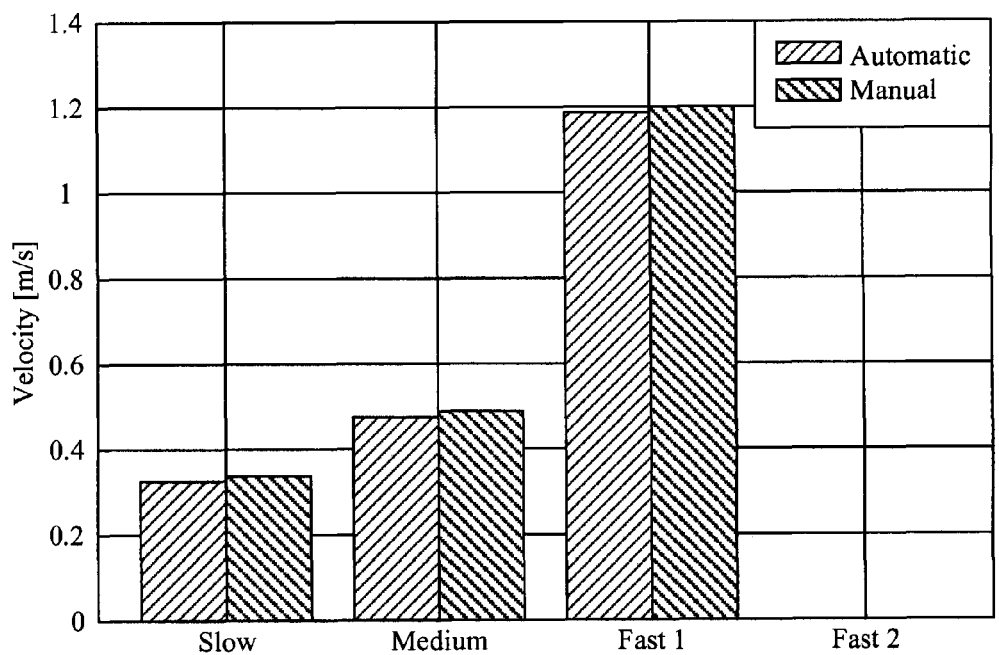
FIGS. 7 and 8 are bar charts of examples of measurements for human subjects according to an embodiment.
Figure 8:
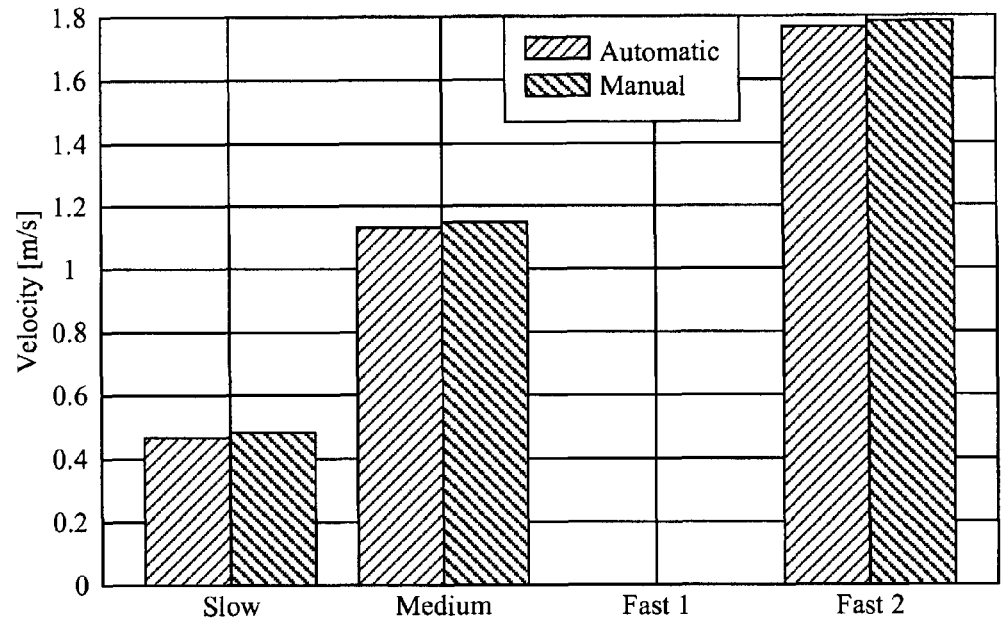

Subjects 1 and 2 did not perform Fast Walk 2. This is denoted by "NC" (not completed). FIG. 7 shows a chart 64 of the results from Subject 1, and FIG. 8 shows a chart 66 of the results from Subject 5. The results demonstrate that there is an unexpectedly excellent agreement (intraclass correlation coefficient, ICC(2,k)>0.99 in all cases) between velocity values manually derived from the server timestamps and those derived automatically using the techniques described herein. This suggests that these techniques may be adequate for use in automatically deriving velocity values from data obtained in the course of a home deployment. It should be noted however that 6 of the 18 recorded walks were deemed incomplete. This may be considered a significant proportion of the walks recorded in this experiment and would appear to be a failing of the PIR sensor type used in this experiment. Accordingly, sensors other than PIR sensors might be used to further improve accuracy. For example, optical (e.g., laser- or light emitting diode-based), motion, radar, biometric, and other types of sensors may also be used.

Figure 9:
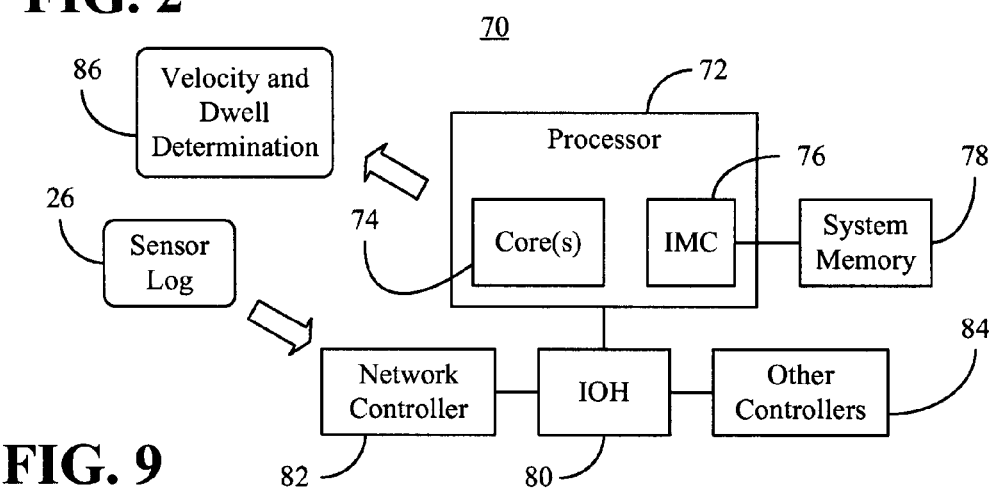
FIG. 9 is a block diagram of a computing system according to an embodiment.

Turning now to FIG. 9, a computing system 70 is shown having a processor 72, system memory 78, an input/output hub (IOH) 80, a network controller 82, and various other controllers 84. Part or all of the system 70 could be incorporated into a velocity rail 16 (FIG. 2), a data aggregator, or other platform. The system 70 could also be part of a mobile platform such as a laptop, personal digital assistant (PDA), wireless smart phone, media player, imaging device, etc., or any combination thereof. In addition, the system 70 may also be part of a fixed platform such as a personal computer (PC), server, workstation, etc. Thus, the processor 72 may include one or more processor cores 74 capable of executing a set of stored instructions, and an integrated memory controller (IMC) 76 configured to communicate with the system memory 78. The system memory 78 could include dynamic random access memory (DRAM) configured as a memory module such as a dual inline memory module (DIMM), a small outline DIMM (SODIMM), etc.

The illustrated IOH 80, sometimes referred to as a Southbridge of a chipset, functions as a host device and communicates with the network controller 82, which could provide off-platform communication functionality for a wide variety of purposes such as cellular telephone (e.g., W-CDMA (UMTS), CDMA2000 (IS-856/IS-2000), etc.), WiFi (e.g., IEEE 802.11, 1999 Edition, LAN/MAN Wireless LANS), Low-Rate Wireless PAN (e.g., IEEE 802.15.4-2006, LR-WPAN), Bluetooth (e.g., IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), and other radio frequency (RF) telephony purposes. In the illustrated example, the network controller 82 obtains a sensor log 26 wirelessly (e.g., from a data aggregator over a Bluetooth connection), and provides the sensor log 26 to the processor 72 for further analysis. The illustrated processor 72 generates in-home gait velocity and dwell time determinations 86, which might include velocity values 50 (FIG. 5) and dwell time 62 (FIG. 6), as already discussed.

The other controllers 84 could communicate with the IOH 80 to provide support for user interface devices such as a display, keypad, mouse, etc. in order to allow a user to interact with and perceive information from the system 70.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

The term "coupled" is used herein to refer to any type of relationship, direct or indirect, between the components in question, and may apply to electrical, mechanical, fluid, optical, electromagnetic, electromechanical or other connections. In addition, the terms "first", "second", etc. are used herein only to facilitate discussion, and carry no particular temporal or chronological significance unless otherwise indicated.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A non-transitory computer-readable medium comprising a set of stored instructions which, if executed, cause an apparatus to:
    receive sensor data,
    identify a first set of entries in the sensor data having a predefined sequence of sensor identifiers, wherein each of the first set of entries has a timestamp, and wherein the first set of entries define a velocity event;
    identify a second set of entries in the sensor data having a sensor identifier that corresponds to a dwell sensor mounted in a doorway and configured to detect a presence of a subject, wherein the second set of entries define a dwell event that corresponds to a duration of time defined by a threshold; and
    calculate at least one of an in-home gait velocity for the velocity event and an in-home dwell time for the dwell event.

2. The non-transitory computer-readable medium of claim 1, wherein the instructions, if executed, further cause the apparatus to calculate in-home gait velocity based on an initial timestamp in the velocity event, a final timestamp in the velocity event, and a distance between sensors corresponding to the initial and the final timestamps.

3. The non-transitory computer-readable medium of claim 2, wherein the instructions, if executed, further cause the apparatus to average a plurality of velocity value calculations, wherein each velocity calculations correspond to a pair of sensors in the predefined sequence.

4. The non-transitory computer-readable medium of claim 2, wherein the instructions, if executed, further cause the apparatus to disqualify the velocity event if a velocity disqualification condition is true, wherein the velocity disqualification condition includes at least one of:
    the in-home gait velocity exceeds a velocity threshold; and
    a time difference between the initial timestamp and the final timestamp of a previous velocity event is less than a velocity reset threshold.

5. The non-transitory computer-readable medium of claim 1, wherein the second set of entries comprise a rising edge timestamp comprising a time indicative of an entrance into a vicinity of the dwell sensor and a falling edge timestamp comprising a time indicative of an exit from a vicinity of the dwell sensor, and wherein the instructions, if executed, further cause the apparatus to calculate the in-home dwell time based on the rising and the falling edge timestamps.

6. The non-transitory computer-readable medium of claim 5, wherein the instructions, if executed, further cause the apparatus to disqualify a dwell event if a dwell event disqualification condition is true, wherein the dwell event disqualification condition includes at least one of:
    a time difference between the rising edge timestamp of the second set of entries and a falling edge timestamp of a previous dwell event is less than a dwell reset threshold;
    the time difference between the rising and falling edge timestamps of the second set of entries exceeds a dwell duration threshold; and
    the time difference between the rising and falling edge timestamps of the second set of entries is a negative value.

7. An apparatus comprising:
    a wall-mounted support having a plurality of sensors mounted thereon, wherein each of the plurality of sensors is configured to generate a timestamp based on a detected entry or exit of a subject from the field of sensitivity of the sensor; and
    a processor configured to:
        receive data from the plurality of sensors; and
        calculate at least one of a gait velocity and a dwell time of the subject based on the timestamps from the plurality of sensors.

8. The apparatus of claim 7, wherein the plurality of sensors share a common clock.

9. The apparatus of claim 7, wherein the plurality of sensors comprise passive infrared sensors, optical sensors, motion sensors, radar-based sensors, biometric sensors, or any combination thereof.

10. The apparatus of claim 7, wherein the plurality of sensors are mounted on the wall-mounted support at known distances.

11. The apparatus of claim 7, wherein the processor is at a location remote from the wall-mounted support.

12. The apparatus of claim 11, further comprising a wireless transmitter configured to transmit data from the plurality of sensors to the processor.

13. The apparatus of claim 7, further comprising a non-transitory memory configured to store data generated by the plurality of sensors.

14. The apparatus of claim 7, wherein the processor is further configured to:
    identify a set of entries in the data from the plurality of sensors having a predefined sequence of sensor identifiers, the set of entries defining a velocity event; and
    calculate an in-home gait velocity from the velocity event.

15. The apparatus of claim 14, wherein the processor is further configured to calculate in-home gait velocity based on an initial timestamp in the velocity event, a final timestamp in the velocity event, and a distance between sensors corresponding to the initial and the final timestamps.

16. The apparatus of claim 15, wherein the processor is further configured to disqualify the velocity event if a velocity disqualification condition is true, wherein the velocity disqualification condition includes at least one of:
    the in-home gait velocity exceeds a velocity threshold; and
    a time difference between the initial timestamp and the final timestamp of a previous velocity event is less than a velocity reset threshold.

17. The apparatus of claim 7, wherein the processor is further configured to:
    identify a second set of entries in the data from the plurality of sensors having a sensor identifier that corresponds to a dwell sensor mounted in a doorway and configured to detect a presence of a subject, the second set of entries defining a dwell event that corresponds to a duration of time defined by a threshold; and
    calculating an in-home dwell time for the dwell event.

18. The apparatus of claim 17, wherein the second set of entries comprise a rising edge timestamp comprising a time indicative of an entrance into a vicinity of the dwell sensor and a falling edge timestamp comprising a time indicative of an exit from a vicinity of the dwell sensor, and wherein the instructions, if executed, further cause the apparatus to calculate the in-home dwell time based on the rising and the falling edge timestamps.

19. The apparatus of claim 18, wherein the processor is further configured to disqualify a dwell event if a dwell event disqualification condition is true, wherein the dwell event disqualification condition includes at least one of:
- a time difference between the rising edge timestamp of the second set of entries and a falling edge timestamp of a previous dwell event is less than a dwell reset threshold;
- a time difference between the rising and falling edge timestamps of the second set of entries exceeds a dwell duration threshold; and
- a time difference between the rising and falling edge timestamps of the second set of entries is a negative value.

20. A non-transitory computer-readable medium comprising a set of stored instructions which, if executed cause an apparatus to:
- receive sensor data;
- identify a set of entries in the sensor data having a predefined sequence of sensor identifiers, the set of entries defining velocity event; and
- calculate an in-home gait velocity for the velocity event.

21. An apparatus comprising a processor configured to:
- receive sensor data;
- identify a set of entries in the sensor data having a predefined sequence of sensor identifiers, the set of entries defining velocity event; and
- calculate an in-home gait velocity for the velocity event.

* * * * *